US010165906B1

(12) United States Patent
Beychok et al.

(10) Patent No.: US 10,165,906 B1
(45) Date of Patent: *Jan. 1, 2019

(54) APPARATUS FOR DISSOLVING A FRAGRANCE CARRIER

(71) Applicant: REMARKABLY WELL, INC, Atlanta, GA (US)

(72) Inventors: Alan M. Beychok, Atlanta, GA (US); Kathleen E. R. Huthmaker, McKinney, TX (US); Todd J. Huthmaker, McKinney, TX (US); Craig J. Cochran, Atlanta, GA (US); Adam D. Ambrecht, Kennesaw, GA (US); Maureen E. Carroll, Atlanta, GA (US); Stephen D. M. Jones, Sandy Springs, GA (US)

(73) Assignee: REMARKABLY WELL, INC, Atlanta, GA (US)

( * ) Notice: Subject to any disclaimer, the term of this patent is extended or adjusted under 35 U.S.C. 154(b) by 0 days.

This patent is subject to a terminal disclaimer.

(21) Appl. No.: 15/972,786

(22) Filed: May 7, 2018

Related U.S. Application Data

(63) Continuation-in-part of application No. 15/691,281, filed on Aug. 30, 2017, now Pat. No. 10,010,643.

(51) Int. Cl.
*A47K 5/00* (2006.01)
*A47K 17/00* (2006.01)
(Continued)

(52) U.S. Cl.
CPC ............... *A47K 5/00* (2013.01); *A47K 17/00* (2013.01); *A61L 9/01* (2013.01); *A61L 9/012* (2013.01);
(Continued)

(58) Field of Classification Search
CPC ... A61L 9/12; A61L 9/012; A61L 9/05; A61L 9/01; A47K 3/281; B05B 1/14; B05B 7/2462
(Continued)

(56) References Cited

U.S. PATENT DOCUMENTS 1,751,524 A 3/1930 Moss
1,945,701 A 2/1934 Pearl
(Continued)

FOREIGN PATENT DOCUMENTS

JP H038459 A1 1/1991
WO 0149421 A1 7/2001
(Continued)

OTHER PUBLICATIONS https://www.etsy.com/listing/497178378/lavender-shower-tablets-aromatherapy?utm_campaign=shopping_us_NaturalAcorn_sfc_osa&utm_medium=cpc&utm_source=google&utm_custom 1=0&utm_content=14309925&gclid=EAIaIQobChMIy-6RyOD_1QIVIoRpCh2ATAkJEAYYASABEgLWq_D_BwE, Aug. 29, 2017, 3 pgs.
(Continued)

*Primary Examiner* — Steven J Ganey
(74) *Attorney, Agent, or Firm* — Pearne & Gordon LLP

(57) ABSTRACT

An apparatus for dissolving a fragrance carrier such as a shower tablet, including a fragrance carrier holder and a mount bracket supporting a water-holding reservoir and configured so that water in the reservoir or from the reservoir can contact and dissolve the fragrance carrier on the holder. The apparatus is attachable to a vertical wall for a shower stall. The reservoir can be provided with a valve to at least partially control flow of water from the reservoir. The valve is preferably a flapper valve, a rotatable flow regulator valve,
(Continued)

a poppet valve or a duckbill valve. A method of dissolving the fragrance carrier is also provided.

24 Claims, 15 Drawing Sheets

(51) Int. Cl.
*A61L 9/12* (2006.01)
*A61L 9/012* (2006.01)
*A61L 9/05* (2006.01)
*A61L 9/01* (2006.01)
*F16B 11/00* (2006.01)
*F16B 47/00* (2006.01)
*F16M 13/02* (2006.01)

(52) U.S. Cl.
CPC .................... *A61L 9/05* (2013.01); *A61L 9/12* (2013.01); *F16B 11/006* (2013.01); *F16B 47/00* (2013.01); *F16M 13/02* (2013.01)

(58) Field of Classification Search
USPC .... 239/6, 10, 34, 37, 38, 43, 273, 282, 289, 239/302, 310, 314, 379, 569; 4/596, 601, 4/605, 615, 661, 663, 903; 222/420, 422
See application file for complete search history.

(56) References Cited

U.S. PATENT DOCUMENTS

| | | | |
|---|---|---|---|
| 1,973,319 A | | 9/1934 | Nelson |
| 2,647,797 A | | 8/1953 | Moss |
| 2,986,340 A | | 5/1961 | Webb |
| 3,018,969 A | | 1/1962 | Gentry |
| 3,180,579 A | * | 4/1965 | Tomaso ................. E03C 1/046 239/310 |
| 3,777,982 A | | 12/1973 | Britton |
| 4,211,368 A | | 7/1980 | Legros et al. |
| D270,468 S | | 9/1983 | Hoyt |
| 4,438,010 A | | 3/1984 | Lindauer et al. |
| 4,580,751 A | | 4/1986 | Panzer |
| 5,025,919 A | | 6/1991 | Brinker et al. |
| 5,029,786 A | | 7/1991 | Wu |
| 5,238,915 A | | 8/1993 | Fuwa et al. |
| 5,274,858 A | * | 1/1994 | Berry ..................... A47K 3/281 239/314 |
| 5,957,387 A | | 9/1999 | Porta et al. |
| 5,993,854 A | | 11/1999 | Needleman et al. |
| 6,006,374 A | | 12/1999 | Winnett et al. |
| D420,464 S | | 2/2000 | Binstock et al. |
| D426,806 S | | 6/2000 | Buckle |
| 6,121,215 A | | 9/2000 | Rau |
| 6,244,778 B1 | | 6/2001 | Chesbrough |
| D473,669 S | | 4/2003 | Hille et al. |
| 6,550,735 B1 | | 4/2003 | Zheng |
| 6,557,782 B1 | | 5/2003 | Urra |
| 6,901,609 B2 | | 6/2005 | Hill |
| 7,093,775 B1 | | 8/2006 | Bingham |
| 7,207,464 B2 | | 4/2007 | Brenner |
| 7,220,436 B2 | | 5/2007 | Rau |
| D565,715 S | | 4/2008 | Wu |
| D602,141 S | | 10/2009 | Harris |
| D620,576 S | | 7/2010 | Jorgensen |
| 7,975,936 B2 | | 7/2011 | Paoluccio |
| 8,007,842 B2 | | 8/2011 | Rau |
| 8,028,933 B2 | | 10/2011 | Friis |
| 8,206,686 B2 | | 6/2012 | Rau |
| D680,879 S | | 4/2013 | Gershune et al. |
| D681,182 S | | 4/2013 | Tomas Vilarasa et al. |
| D692,116 S | | 10/2013 | Gordon |
| 8,566,972 B2 | | 10/2013 | Vogtner et al. |
| D713,518 S | | 9/2014 | Carbone et al. |
| 8,820,660 B2 | | 9/2014 | Ajagbe |
| 8,955,536 B2 | | 2/2015 | Bell |
| 9,085,006 B2 | | 7/2015 | Wu et al. |
| 9,115,884 B2 | | 8/2015 | White |
| 9,200,667 B1 | | 12/2015 | Hsu |
| 9,211,994 B2 | | 12/2015 | Andersen et al. |
| D750,314 S | | 2/2016 | Hobson et al. |
| D801,509 S | | 10/2017 | Weening et al. |
| 10,010,643 B1 | | 7/2018 | Beychok |
| 2008/0146487 A1 | | 6/2008 | O'Connor et al. |
| 2009/0101733 A1 | | 4/2009 | Popov et al. |
| 2010/0040774 A1 | | 2/2010 | Russell |
| 2010/0199420 A1 | | 8/2010 | Lee |
| 2012/0283668 A1 | | 11/2012 | Shalev |
| 2014/0001027 A1 | | 1/2014 | Balass |
| 2014/0315719 A1 | | 10/2014 | Rau et al. |
| 2015/0053790 A1 | | 2/2015 | Hanna et al. |
| 2016/0243565 A1 | | 8/2016 | Batista |
| 2016/0287471 A1 | | 10/2016 | Urfig |
| 2016/0354306 A1 | | 12/2016 | Rau et al. |

FOREIGN PATENT DOCUMENTS

| | | | |
|---|---|---|---|
| WO | 2005063104 A1 | 7/2005 | |
| WO | 2010093947 A2 | 8/2010 | |

OTHER PUBLICATIONS http://www.ulta.com/luxe-aromatherapy-shower-tablets?productId=xlsImpprod15541099&sku=2503770&cmpid=PS_Non!google!Product_Listing_Ads&cagpspn=pla&CATCI=aud-297352281988: pla-297761130689&CAAGID=39172131008&CAWELAID=330000200001096929&catargetid=330000200001152683&cadevice=c&gclid=EAIaIQobChMIy-6RyoD_1QIVIoRpCh2ATAkJEAYYAiABEgJQjPD_BwE , Aug. 29, 2017, 2 pgs.

https://www.etsy.com/listing/509485540/small-bath-bomb-shower-tablet-orange?utm_campaign=shopping_us_HandmadeBeautyByLu_sfc_osa&utm_medium=cpc&utm_source=google&utm_custom1=0&utm_content=14926788&gclid=EAIaIQobChMIy-6RyoD_1QIVIoRpCh2ATAkJEAYYBSABEgIQRvD_BwE , Aug. 29, 2017, 3 pgs.

https://www.etsy.com/listing/269884683/shower-steamers-shower-fizzies-shower?gp1a=1&gao=0&utm_campaign=shopping_us_BathThymeBoutique_sfc_osa&utm_medium=cpc&utm_source=google& utm_custom1=0&utm_content=11179150&gclid=EAIaIQobChMIy7au1OH_1QIVkLXACh32ywGwEAQYCCABEgITBfD_BwE, Aug. 29, 2017, 4 pages.

https://www.etsy.com/listing/514028380/menthol-shower-tablets?gpla=1&gao=0&utm_campaign=shopping_us_PrettiesByJudi_sfc_osa&utm_medium=cpc&utm_source=google&utm_custom 1=0&utm_content=7095078&gclid=EAIaIQobChMIy7au1OH_1QIVkLXACh32ywGwEAQYCyABEgKIR_D_BwE , Aug. 29, 2017, 3 pages.

https://www.etsy.com/listing/273505698/shower-steamer-shower-bombs-shower-melts?gpla=1&gao=l&utm_campaign=shopping_us_FizzleSoap_sfc_osa&utm_medium=cpc&utm_source=google&utm_cusom1=0&utm_content=12272935&gclid=EAIaIQobChMIy7au1OH_1QIVkLXACh32ywGwEAQYDiABEgK8bPD_BwE , Aug. 29, 2017, 7 pages.

https://www.bedbathandbeyond.com/store/product/aura-cacia-reg-3-count-aromatherapy-shower-tablets-in-relaxing-lavender/1017847767?skuId=17847767&mcid=PS_googlepla_nonbrand_beautywellness_online&product_id=17847767&adtype=pla_multichannel&product_channel=online&adpos=1o4&creative=43742630269&device=c&matchtype=&network=g&gclid=EAIaIQobChMIy-6RyoD_1QIVIoRpCh2ATAkJEAYYBCABEgJPLfD_BwE , Aug. 29, 2017, 3 pages.

https://www.iherb.com/pr/Aromatherapaes-De-Stress-Spa-Shower-Tablets-Neroli-Chamomile-6-Aromatherapy-Tablets-8-oz-23-g-Each/66701?ccode=us&currcode=USD&langcode=en-US&gclid=EAIaIQobChMIy7au1OH_1QIVkLXACh32ywGwEAQYCSABEgJWy_D_BwE, Aug. 29, 2017, 2 pages.

(56) References Cited

OTHER PUBLICATIONS http://www.smallflower.com/patisserie-de-bain/lavender-bath-melt-45g-bath-tablets-10071098?utm_source=google&utm_medium=cpc&utm_campaign=sidecar&adpos=1o10&scid=scplp10071098&sc_intid=10071098&gclid=EAlaIQobChMly7au1OH_1QIVkLXACh32ywGwEAQYCiABEgKhefD_BwE , Aug. 29, 2017, 1 page.
ULTA Inc., Aromatherapy Shower Tablets, Aug. 9, 2017, 4 pages.
OnZen, OnZen Premium Shower Head, Aug. 29, 2017, 5 pages.
OPUS International LLC, Luxury Shower Head—Aroma Sense, Aug. 29, 2017, 4 pages.
Sigex Limited (HK), Cyclone Spa—Mineral Spa Shower System, Aug. 29, 2017, 2 pages.
Steam Spa, SteamSpa Steamhead with Aromatherapy Reservoir, Aug. 29, 2017, 4 pages.
https://www.etsy.com/listing/293287467/aromatherapy-shower-steamers?ref=pr_shop , Aug. 29, 2017, 3 pages.
http://www.ebay.es/itm/SPA-HOT-TUB-SPAZAZZ-AROMA-THERAPY-EFFERVESCENT-TABLETS-BOX-OF-12-/251902295552 , Aug. 29, 2017, 1 page.
Top Shelf Lacquer, Shower Bombs—Eucalyptus & Menthol, Aug. 29, 2017, 2 pages.
Chlorine Tablets reference found online [Jul. 21, 2018]—http://www.tradekorea_com/product/detail/P233234/Chlorine-Tablets,-Chlorine-Granules,-Chlorine-Powder.html.

\* cited by examiner

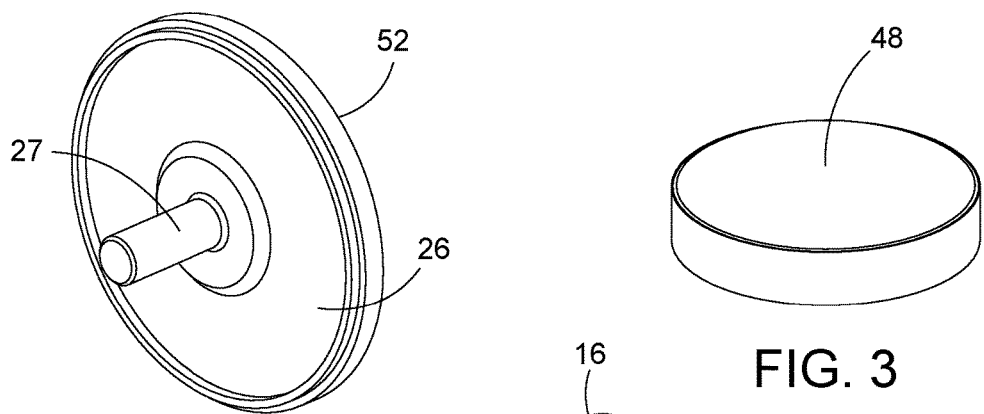
FIG. 2
FIG. 3
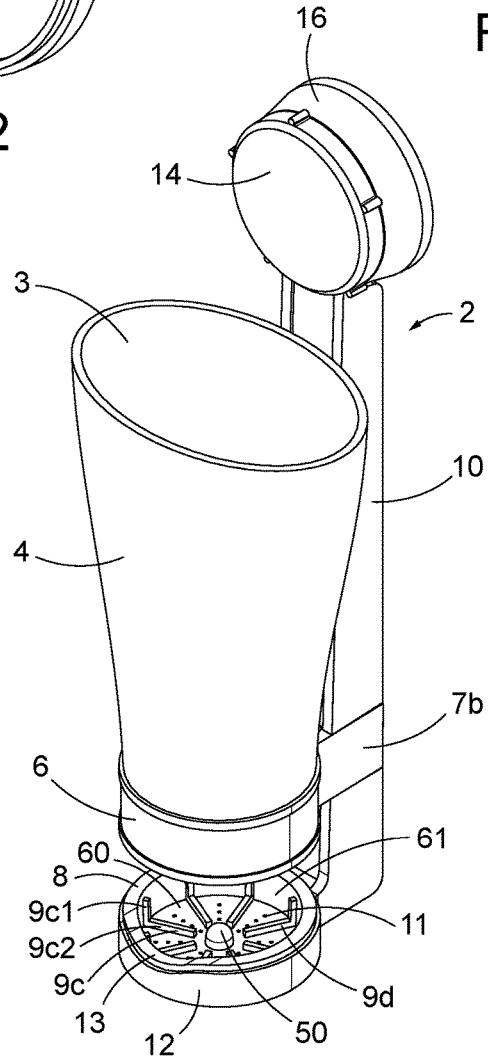
FIG. 4

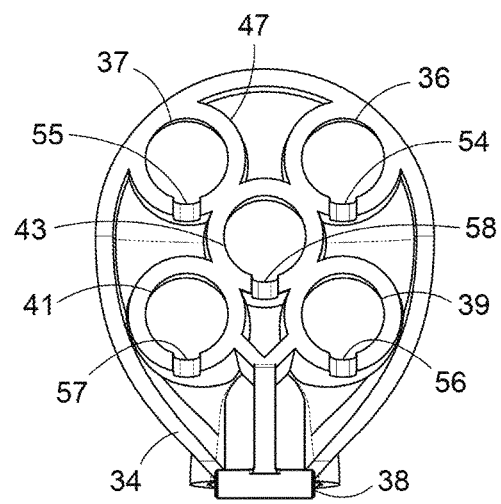
FIG. 9
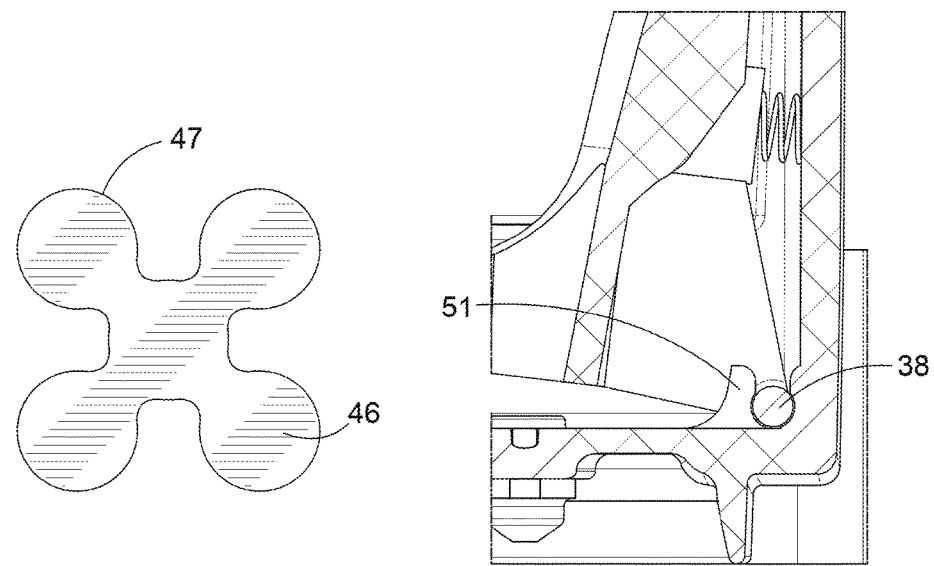
FIG. 10
FIG. 11

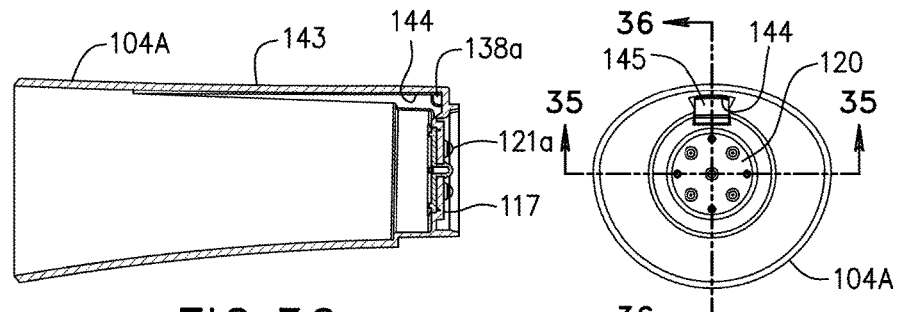
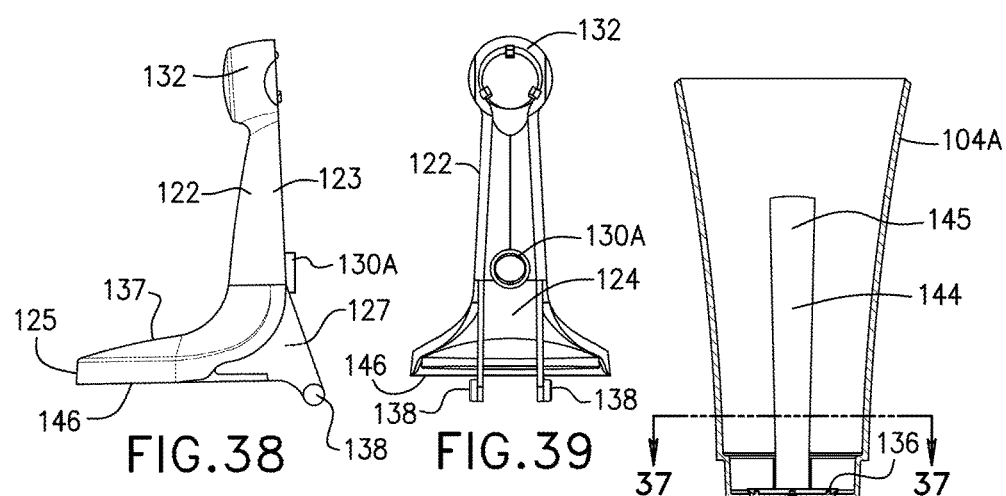
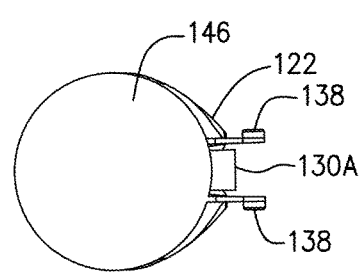
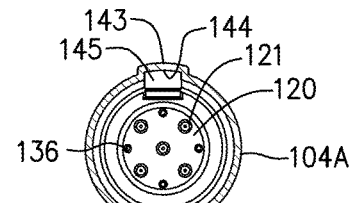

APPARATUS FOR DISSOLVING A FRAGRANCE CARRIER

FIELD OF THE INVENTION

The present invention relates to an apparatus for dissolving a fragrance carrier, preferably a shower tablet, in a shower or bath.

DESCRIPTION OF RELATED ART

US 2008/0146487 A1 teaches a tablet about the size of a small hockey puck which is thrown into the bathtub or onto the floor of a shower stall. The bath water or water from the shower head dissolves the tablet and releases aroma and fragrances. Typically, the tablet is effervescent. Bath bombs are also known, which are placed in bathwater to add essential oils, scent, bubbles and color to the bathwater. There is a need for an apparatus which holds the fragrance carrier and keeps it out of the bathwater and off the floor of the shower stall, so it won't be stepped or sat on and so that dissolution of the fragrance carrier can preferably be controlled and/or slowed down.

BRIEF DESCRIPTION OF THE DRAWINGS

FIG. 2 is a perspective view of a mount anchor;

FIG. 3 is a perspective view of a fragrance carrier or shower tablet for use with the apparatus of FIGS. 1 and 4 and other apparatuses according to the invention;

FIG. 4 is a perspective view of the apparatus of FIG. 1 in an assembled and operating condition;

FIG. 9 is a bottom plan view of the valve 22;

FIG. 10 is a top plan view of a valve membrane;

FIG. 11 is a view similar to a central portion of FIG. 6, showing the pivot and pivot seating;

FIG. 34 is a top plan view of the water-holding reservoir of FIG. 30;

FIG. 35 is a cross-sectional view taken along line 35-35 of FIG. 34;

FIG. 36 is a cross-sectional view taken along line 36-36 of FIG. 34;

FIG. 37 is a cross-sectional view taken along line 37-37 of FIG. 35 wherein the cross-sectional view in FIG. 37 includes both halves of the apparatus of FIG. 35;

FIG. 38 is a left side view of the flapper valve of FIG. 29;

FIG. 39 is a back view of the flapper valve of FIG. 38; and

FIG. 40 is a bottom plan view of the flapper valve of FIG. 38.

SUMMARY OF THE INVENTION

An apparatus for dissolving a fragrance carrier, the apparatus comprising a mount bracket, a water-holding reservoir and a fragrance carrier holder, the water-holding reservoir being supported by the mount bracket, the fragrance carrier holder being provided in association with the water-holding reservoir such that (a) water in the water-holding reservoir can contact and dissolve a fragrance carrier located on the fragrance carrier holder, the fragrance carrier holder being located inside the water-holding reservoir, or (b) water can flow from the water-holding reservoir to contact and dissolve a fragrance carrier located on the fragrance carrier holder. The apparatus is configured and adapted so that it is attachable to a vertical wall of a shower stall by suction or adhesive. The water-holding reservoir preferably has one or more drain openings at a bottom of the water-holding reservoir. A method for dissolving a fragrance carrier is also provided.

DETAILED DESCRIPTION OF PREFERRED EMBODIMENTS OF THE INVENTION

In the description that follows, when a preferred range, such as 5 to 25 (or 5-25) is given, this means preferably at least 5 and, separately and independently, preferably not more than 25.

Figure 24:
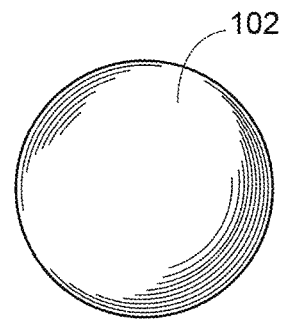
FIG. 24 is a schematic top view illustration of an alternative embodiment of a fragrance carrier.
Figure 25:
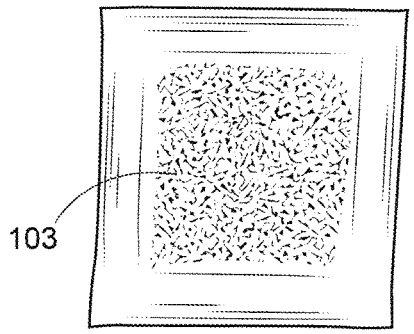
FIG. 25 is a schematic top view illustration of an alternative embodiment of a fragrance carrier inside a filter bag.
Figure 26:
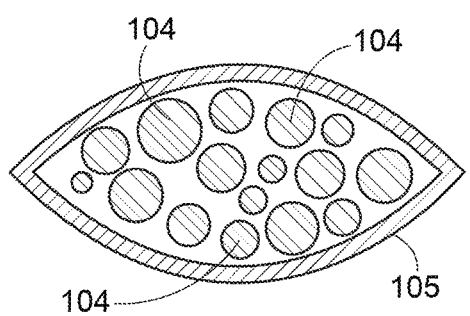
FIG. 26 is a schematic cross-sectional side view of an alternative embodiment of a fragrance carrier inside a mesh bag.
Figure 27:
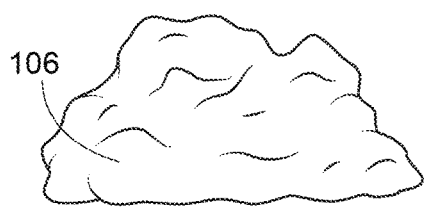
FIG. 27 is a schematic side view illustration of an alternative embodiment of a fragrance carrier.
Figure 28:
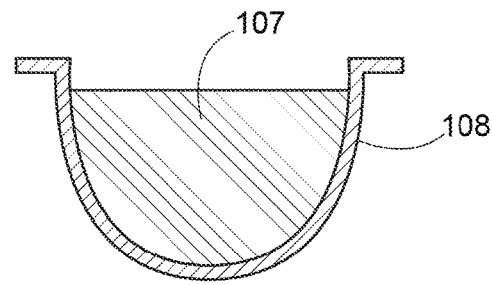
FIG. 28 is a schematic cross-sectional side view of an alternative embodiment of a fragrance carrier in a cup.

With reference to FIGS. 1 and 4-6, there is shown a preferred embodiment of the invention, that is, an apparatus 2 (preferably made of plastic or metal) for dissolving a fragrance carrier. In the present invention, the fragrance carrier carries the fragrance and releases the fragrance into the shower or bath area as the fragrance carrier dissolves in water. The fragrance carrier is preferably a shower tablet 48 as known in the art, preferably a fragranced shower tablet or an effervescent or non-effervescent shower tablet or an aromatherapy shower tablet as known in the art, which has a composition as known in the art, for example comprising sodium bicarbonate, citric or adipic acid, maltodextrin and fragrance such as perfume. As known in the art, when water contacts the shower tablet, it fizzes or effervesces and releases the fragrance into the shower and surrounding bathroom, energizing, refreshing and/or calming the user; the fragrance can also be directed for enhancing or transforming the mood of the user. Optionally, the shower tablet can be a shower tablet for therapeutic purposes including but not limited to sinus decongestion via vapors released from the shower tablet. The shower tablet 48 is preferably about 1 to 2, or about 1.5, cm high and 4-6 cm in diameter and weighs about 26-40 g. When the tablet 48 is centered in the cup 8, the distance from the perimeter of the tablet to the front face of the vertical portion (e.g., 9c1) of the ribs is about 1-3 mm, and to the wall 61 is about 2-5 mm. Alternatively, the fragrance carrier can be the same or similar composition as a shower tablet described above, but in the shape of a ball 102 (see FIG. 24) or any other shape or size (powder, small granules, pellets, etc.) or the fragrance carrier can be in the form or shape of a powder or crystals or fragrance salts or small granules in a filter bag 103 (see FIG. 25) which is water-permeable material like a tea bag or sachet bag or fabric bag or the fragrance carrier can be larger granules 104 or pellets 104 or small balls 104 (e.g., 3-10 mm in diameter) in a plastic or fabric mesh bag 105 (FIG. 26), or the fragrance carrier can be a blob of gel 106 (FIG. 27) or a solid or gel 107 in a plastic cup 108 (FIG. 28).

Figure 1:
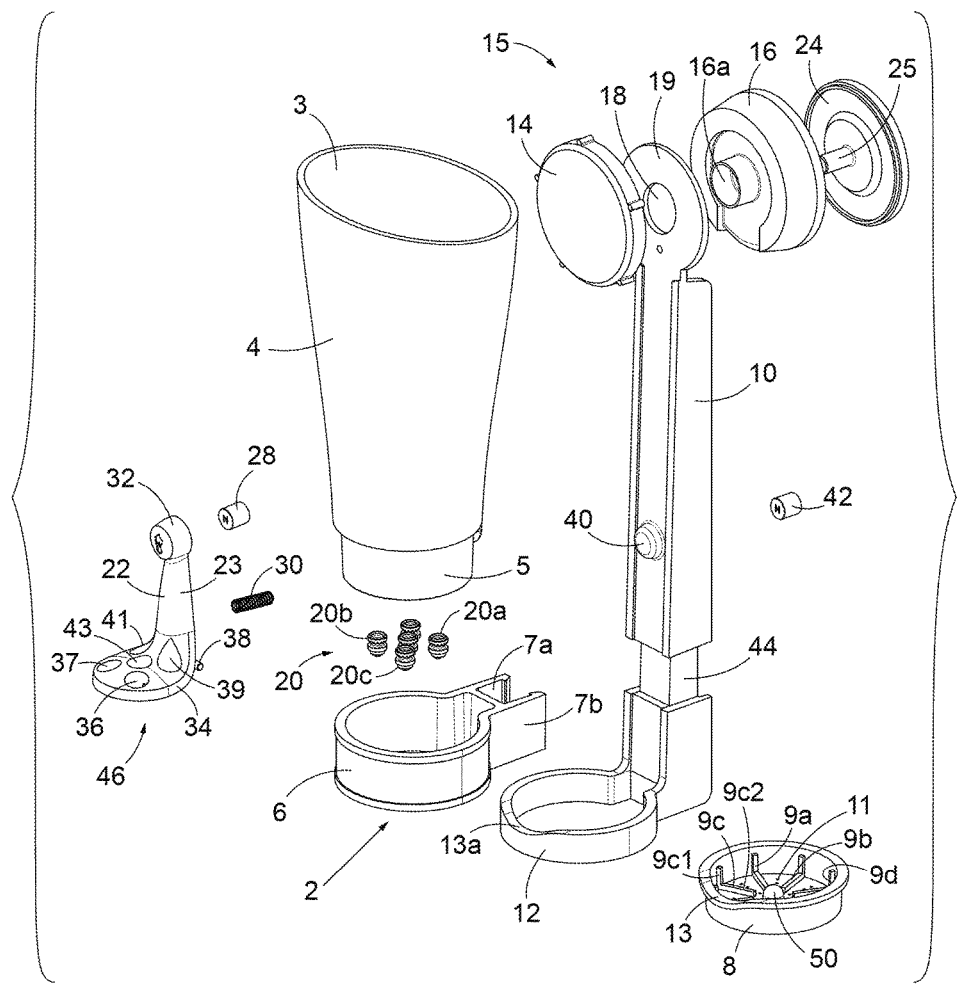
FIG. 1 is an exploded view of an apparatus according to an embodiment of the invention for dissolving a fragrance carrier.
Figure 5:
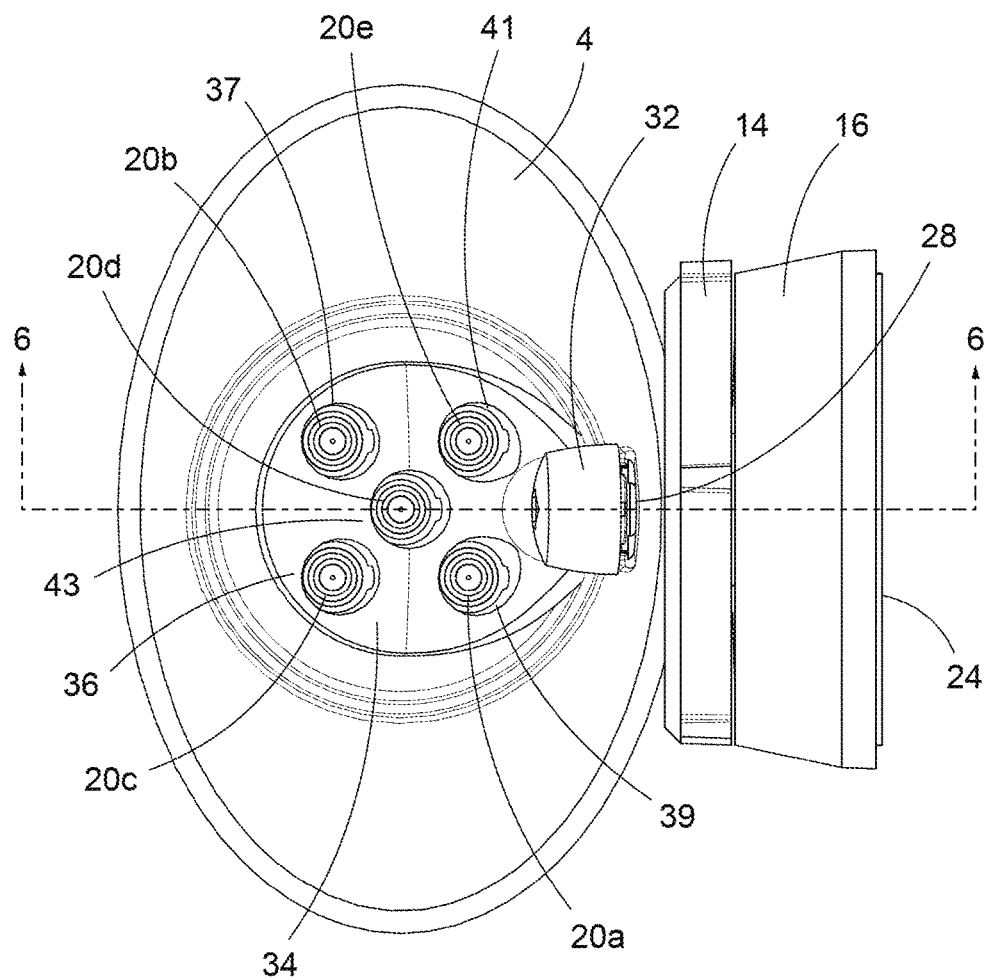
FIG. 5 is a top plan view of the apparatus of FIG. 4.

The apparatus 2 comprises a water-holding reservoir 4 (preferably polycarbonate plastic), a mount bracket 10, a wall mount 15, a reservoir support bracket 6, a fragrance carrier holder or dissolving cup 8 and a fragrance carrier holder support bracket or dissolving cup support bracket 12. The mount bracket comprises the reservoir support bracket and the fragrance carrier holder support bracket or dissolving cup support bracket; all the brackets are preferably plastic or metal. The wall mount 15 can be integral with or part of the mount bracket 10, or separate from mount bracket 10. The reservoir 4 is supported by the mount bracket 10 and has an opening 3 at the top and a narrowed portion 5 at the bottom to engage and seat in the reservoir support bracket 6. Alternatively, support bracket 6 can engage reservoir 4 higher up, such as half-way up reservoir 4, for example via a narrowed portion or via other attachment mechanism. Reservoir 4 is preferably shaped so that it is wider in the upper portion and narrower in the lower portion, or wider the higher it extends up from the bottom, as a funnel-shape, as shown in FIG. 1; this provides a water tower funnel effect, such that water pressure at the bottom is higher for a longer period than if the reservoir was narrower in the upper portion. The bottom of reservoir 4 can be sealed via a valve, such as valve 22, as described later. Support bracket 6 clips to mount bracket 10 at necked-down region 44 via snap arms or latching arms 7a, 7b. Alternatively, bracket 6 can be integrally molded with bracket 10 or attached via other means as known in the art.

Mount bracket 10 can be fixed or mounted in a shower stall or in or above a bathtub, preferably about 4-6 feet (122-183 cm) or about 5 feet (152 cm) above the floor, to a wall or a substantially vertical surface (e.g., tile or wall of a shower stall) via wall mount 15, which preferably comprises a knob 14, a mount housing 16, and a mount suction cup 24. The knob 14 has a hollow internally-threaded central post 14a (see FIG. 12) which extends through hole 18 in the top portion 19 of mount bracket 10, through opening 16a of mount housing 16, and around an externally-threaded post 25 of mount suction cup 24. Knob 14 is rotated to threadingly pull back the central portion of mount suction cup 24 so that mount suction cup 24 will adhere to the wall or tile via suction force, as is known in the art. Optionally, mount housing 16 can be made integrally with portion 19 of mount bracket 10.

Alternatively, instead of mount suction cup 24, there can be used a mount anchor 26 (see FIG. 2) comprising an externally-threaded post 27 (corresponding to post 25) and an adhesive surface 52 so that mount anchor 26 can adhesively adhere to the tile or wall or other surface. Other wall mounts as known in the art can be used to mount the mount bracket 10 on the wall, and the wall mount or any of its parts can optionally be integrally molded or unitary or one piece with the mount bracket.

Figure 6:
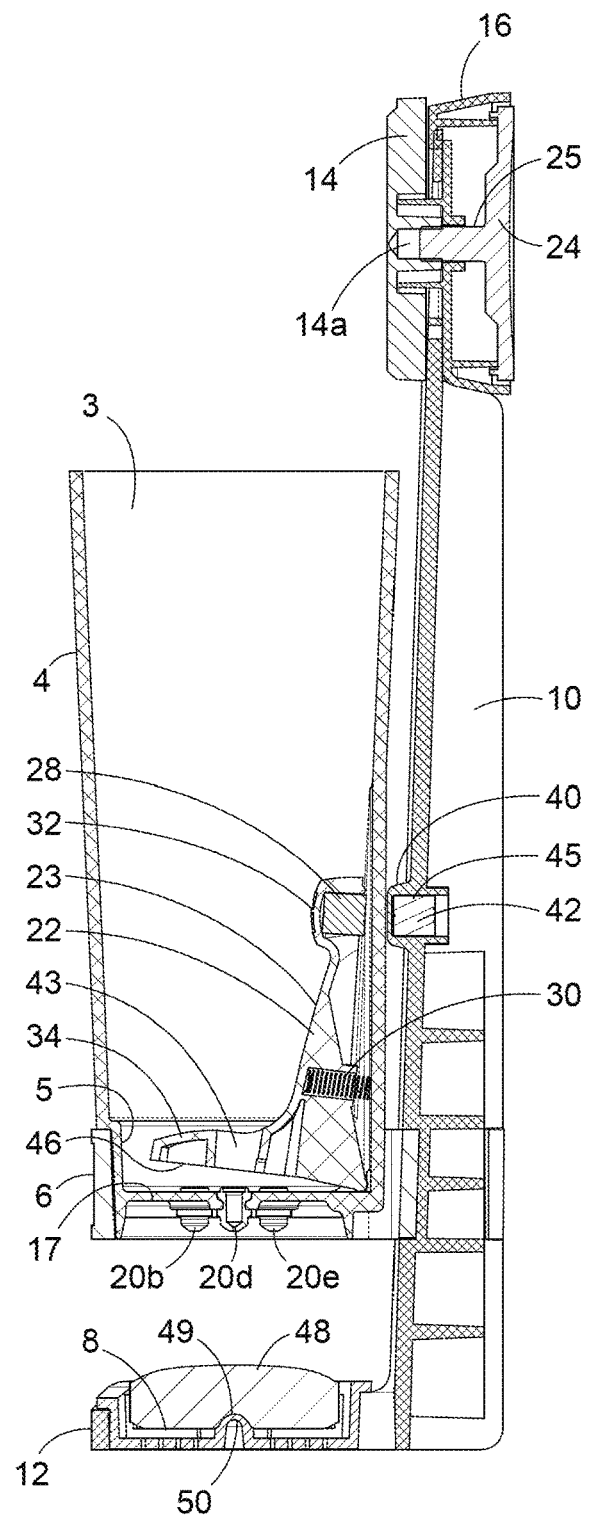
FIG. 6 is a cross-sectional view taken along line 6-6 of FIG. 5.

Fragrance carrier holder support bracket or dissolving cup support bracket 12 can be integrally molded as part of mount bracket 10, or can be molded separately and clipped or otherwise fixed to mount bracket 10 as known in the art. With reference to FIGS. 1, 4 and 6, the fragrance carrier holder or dissolving cup 8 is located beneath the bottom of the reservoir 4 and has a series of standoffs or ribs 9a, 9b, 9c, 9d and others. Each rib (e.g., rib 9c) has a horizontal portion (e.g., 9c2) adjacent the floor 60, and a vertical portion (e.g., 9c1) adjacent the inner perimeter wall 61 of the dissolving cup 8. The ribs keep the fragrance carrier or shower tablet 48 (see FIGS. 3 and 6) spaced apart from the floor 60 and wall 61 of the cup 8 so that more tablet 48 surface area is exposed to the dissolving action of the water. The floor 60 of cup 8 has a series of drain holes or openings 11 (preferably 1-3 mm) (the wall 61 can also have drain holes) and a central protrusion or dome or bump or post or knob 50 which engages a corresponding central cavity 49 (preferably having a shape corresponding to the exterior shape of the protrusion 50) on the bottom of the shower tablet 48. The protrusion 50/cavity 49 helps keep the tablet 48 centered in the cup 8 for more effective dissolution, even as the tablet 48 gets smaller. The dome shape of the protrusion 50/cavity 49 can alternatively be another ornamental shape, such as a cylindrical post, or a post having (in plan view) the shape of a triangle, square, rectangle, oval, star, polygon, bow tie, baseball bat, boomerang, baseball glove, etc.

Figure 19:
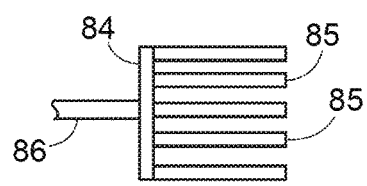
FIG. 19 is a schematic top view illustration of an alternative embodiment of a fragrance carrier holder.
Figure 20:
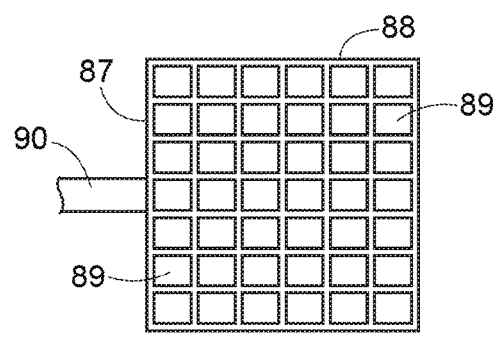
FIG. 20 is a schematic top view illustration of an alternative embodiment of a fragrance carrier holder.
Figure 21:
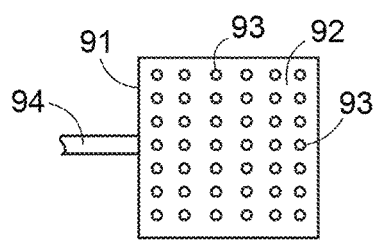
FIG. 21 is a schematic top view illustration of an alternative embodiment of a fragrance carrier holder.
Figure 22:
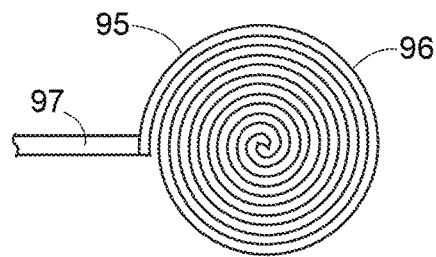
FIG. 22 is a schematic top view illustration of an alternative embodiment of a fragrance carrier holder.
Figure 23:
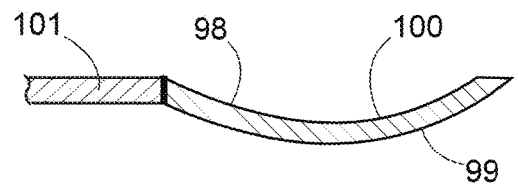
FIG. 23 is a schematic cross-sectional side view of an alternative embodiment of a fragrance carrier holder.

Cup 8 has a lip 13 which is lower than the rest of wall 61, to permit excess water to drain out; support bracket 12 has a corresponding lip 13a. Dissolving cup 8 is a preferred embodiment of a fragrance carrier holder (which is designed and effective to hold a fragrance carrier and permit it to be dissolved by water); other fragrance carrier holders can be used, such as shown in FIGS. 19-23, described as follows. FIG. 19 shows a fragrance carrier holder 84 having a series of prongs or fingers 85 for holding the shower tablet 48 or other fragrance carrier (such as described with reference to FIGS. 24-28). The fragrance carrier holder 84 is attached to the mount bracket 10 by a fragrance carrier holder support bracket, a portion of which is shown at 86; the rest of support bracket 86 is fixed to mount bracket 10 similar or the same as support bracket 12 is attached to mount bracket 10. FIG. 20 shows a fragrance carrier holder 87 comprising a grate 88 having a series of drain holes or drainage openings 89; a portion 90 of the fragrance carrier holder support bracket is also shown. A screen can be used in place of the grate. FIG. 21 shows a fragrance carrier holder 91 comprising a tray or shelf 92 which can have drainage perforations 93 or which can be unperforated; a portion 94 of the fragrance carrier holder support bracket is also shown. FIG. 22 shows a fragrance carrier holder 95 comprising a coil 96 (preferably metal or plastic) for holding the shower tablet 48 or other fragrance carrier; a portion 97 of the fragrance carrier holder support bracket is also shown. FIG. 23 shows a fragrance carrier holder 98 comprising a dish or cup 99 (which is preferably circular or rectangular in plan view and which can be perforated or non-perforated) which has a concave inner surface 100; a portion 101 of the fragrance carrier holder support bracket is also shown. All the fragrance carrier holders can be flat, or can be concave like fragrance carrier holder 98 to better hold the fragrance carrier; all the fragrance carrier holders can optionally have (a) a perimeter wall like perimeter wall 61 and (b) ribs or standoffs like ribs 9a, 9c, etc. A fragrance carrier holder that is sized to effectively hold a shower tablet is a tablet holder.

With reference to FIGS. 1, 5, 6 and 7, the reservoir 4 has a bottom or floor 17 through which extend one or more nozzles 20 (five nozzles are shown, but alternatively there can be 1, 2, 3, 4, 6, 7, 8, 9, 10 or more); these nozzles are drain openings. Before being added to the floor 17, the nozzle can be molded individually or in one or more groups where they are integrally or monolithically joined together via connecting or interconnected arms or similar. The nozzles 20 or nozzle group or groups can be assembled to or co-molded or over molded with floor 17, which is preferably molded with the rest of the reservoir 4. Each nozzle 20 has a central bore, preferably 0.2-1.5, 0.3-1.2, 0.4-1, 0.5-0.8, 0.5-0.7 or about 0.6, mm in diameter, through which the water in the reservoir 4 passes. Alternatively, different nozzles can have different diameter bores; for example, with 5 nozzles, 3 nozzles can have 0.6 mm bores and the other 2 can have 0.5 mm bores, to regulate volume of flow to different parts of a tablet 48 or other fragrance carrier. The drain holes (such as holes 11) in the cup 8 can have a diameter (and/or number of holes) which is a function of the diameter and number of nozzles 20 in the reservoir 4, so that the amount of water held in the cup 8 (inflow minus outflow) is controlled or regulated, to control the amount of water retained and surrounding the tablet 48 or other fragrance carrier, to control or regulate the dissolution rate. The nozzles can also be openings through the floor 17.

The water-holding reservoir is preferably provided with a valve, preferably a valve selected from the group consisting of flapper valves, rotatable flow regulator valves, poppet valves and duckbill valves.

Figure 7:
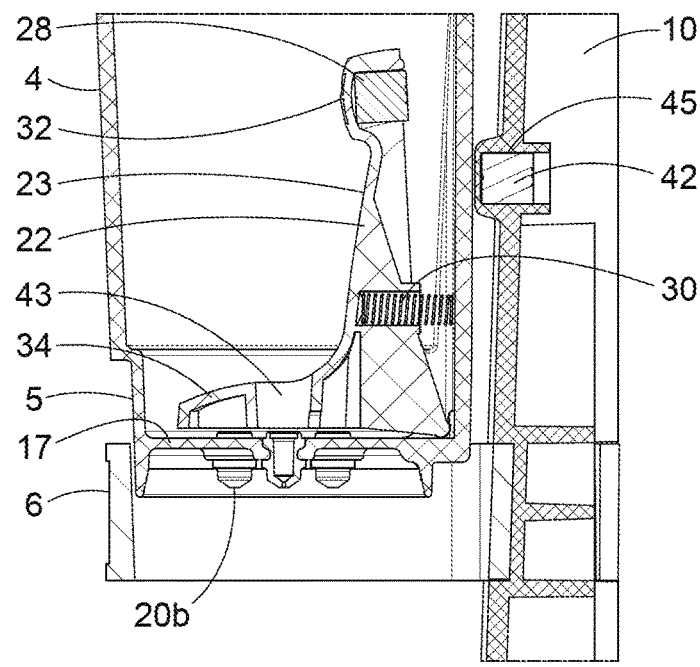
FIG. 7 is a view similar to FIG. 6, but where the bottom or narrowed portion 5 of the reservoir 4 has not been put into the reservoir support bracket 6 and the valve 22 is closed.
Figure 8:
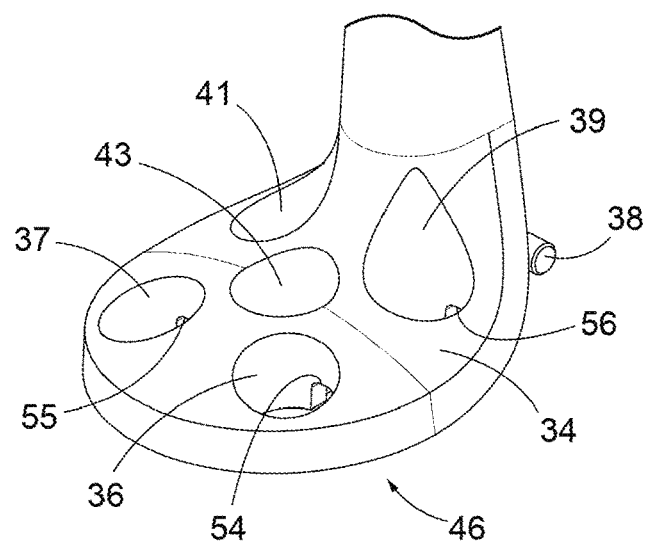
FIG. 8 is a perspective view of the foot 34 of the valve 22.

With reference to FIGS. 1 and 5-11, there is shown a flapper valve 22 comprising a central portion 23, a flapper foot or valve foot 34 and a pivot 38. A valve magnet housing 32 is provided at the top of the central portion 23; a valve magnet or first magnet 28 is constrained or fixed in the housing 32. A plurality of bores 36, 37, 39, 41, 43 are provided in valve foot or flapper foot 34. A resilient and/or elastomeric (or hard or rigid plaster) valve membrane 46 (preferably about 1-2 mm thick) is fixed to the bottom of the foot 34; the top of each nozzle 20 is preferably flat (see FIGS. 1, 7 and 8) so that when the foot 34 is in the closed position as shown in FIG. 7, the valve membrane 46 closes the top of the central bore of each nozzle 20.

At the bottom of each bore 36, 37, 39, 41, 43 (and above the valve membrane 46) there is a respective drain hole 54, 55, 56, 57, 58 which drains water from the bore when the foot 34 is in the open position as shown in FIG. 6. As shown in FIGS. 9-10 and as indicated by the location of valve membrane perimeter 47 in FIGS. 9-10, the valve membrane 46 is sized so that it covers the bottom of each bore 36, 37, 39, 41, 43 and an additional 1-3 mm, to facilitate good sealing with the top of each nozzle 20.

As shown in FIG. 11, pivot 38 snaps into pivot seating 51 so that flapper valve 22 is fixed inside and near the bottom of reservoir 4 and can rotate clockwise/counterclockwise with reference to FIGS. 6, 7, 11. With reference to FIGS. 6-7, valve 22 is spring-biased or spring-loaded such that, when the reservoir 4 is removed from the reservoir support bracket 6 (such as for refilling with water), the spring 30, which is fixed in position between the valve 22 and the wall of reservoir 4, urges the valve 22 to rotate until it closes and clampingly seals, via membrane 46, the central bore at the top of each nozzle 20.

In operation, the shower tablet 48 or other fragrance carrier is positioned in the dissolving cup 8, which is positioned in the dissolving cup support bracket 12. When the user wants to take a shower or bath, the user removes the reservoir 4 from the support bracket 6. The spring 30 then biases the valve 22 to rotate until the membrane 46 presses against the tops of the nozzles 20 and closes them. The user then fills or at least partially fills (such as from the shower head) the reservoir 4 with water (preferably warm or hot), which can't escape because the valve 22 is closed. The user then seats or mounts the bottom or narrowed portion 5 of the reservoir 4 in or on the support bracket 6. In this position (see FIG. 6), the magnet 28, which is fixed in housing 32, is magnetically attracted, due to spatial proximity, to the mount bracket magnet or second magnet 42, which is constrained or fixed in a cavity 45 (behind a nesting bulge 40) located in the mount bracket 10. The magnetic attraction of the magnets 28, 42 overcomes the resistance of the spring 30 and rotates valve 22 towards second magnet 42 (see FIG. 6) so that the foot 34 and membrane 46 lifts or tilts off the nozzles 20, causing the foot 34 to open, opening the central bores of the nozzles 20 so that the water in the reservoir 4 can flow through the nozzles 20 and fall onto the fragrance carrier or tablet 48. The tablet 48 is dissolved primarily by the falling water and may also be partially dissolved by water accumulating in the dissolving cup 8. When the fragrance carrier is 93% dissolved, it is at least substantially dissolved. The water will slowly dissolve the tablet 48 or other fragrance carrier and release its fragrance into the air, providing aromatherapy to the user (this aromatherapy being known in the art). Water can drain through the drain holes 11 and go over the lips 13, 13a, falling into the bath or shower stall. Substantially all the water in the reservoir 4 will flow out; the water in the bores 36, 37, 39, 41, 43 will flow out (due to tilting) through the respective drain holes 54-58 (provided at the base of the flapper foot 34) and then out through the nozzles 20. Preferably the size of the tablet/fragrance carrier 48, the volume of the reservoir 4, the number of nozzles and the diameter of the bore in each nozzle are predetermined so that the tablet 48 completely dissolves shortly (about 10-30 seconds) before the water runs out; preferably the flow is such as to dissolve the tablet 48 in about 1-20 or 3-15 or 7-10 minutes.

The magnets are preferably neodymium or similar, due to the strength thereof. The reservoir 4 is sized to receive a shower tablet therein and preferably holds 0.5 to 1 or 1.5 liters of water and is 15 to 20 cm high, measured from the floor 17. The dissolving cup 8 is preferably 2 to 4 cm in diameter (measuring the diameter of the circle defined by the front faces of the vertical portions of the ribs 9a, 9b, etc. or, less preferably, measuring the diameter of the circle defined by the wall 61) and 0.5 to 1.5 cm high (measured from the tops of horizontal portions such as 9c2 or, less preferably, measured from the floor 60).

Assuming the valve 22 is closed and the reservoir 4 is fully seated in the support bracket 6, the distance between the magnets 28 and 42 is preferably about 1-3 or 1-2 or about 1.5 or about 2 cm.

Other flapper valves can be used, such as a flapper valve which is commonly used in a residential toilet, wherein, for example, the user can pull the chain to open the flapper foot of the flapper valve and then hook the chain, via a hook attached to the chain, on the rim of the reservoir 4 or elsewhere on the apparatus 2, to keep the flapper foot open.

Figures 12, 13:
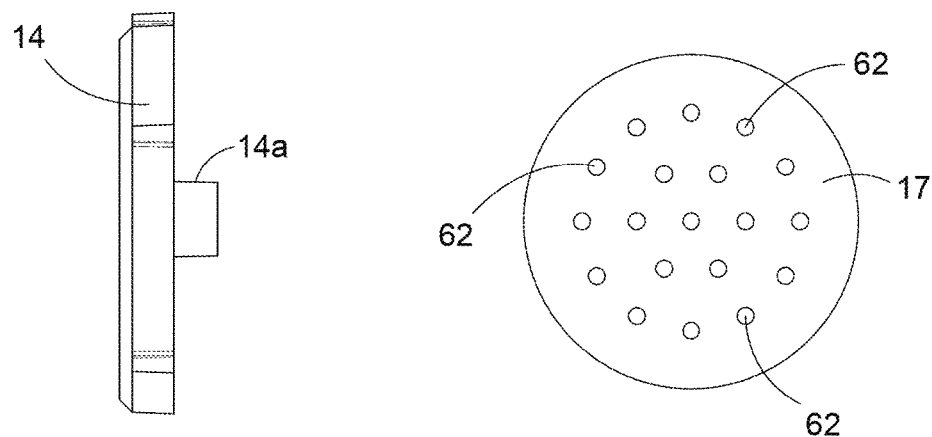
FIG. 12 is a side view of the knob 14.
FIG. 13 is a top plan view of an alternative embodiment of the floor of the reservoir.

Alternatively, the apparatus 2 can be constructed without the presence of a valve such as valve 22. In this case, when the reservoir 4 is filled with water, water begins immediately to flow through the nozzles 20. This is less preferred, since water will flow out of the reservoir 4 as the user is filling the reservoir and transporting it to the bracket 10 and installing it in the support bracket 6, getting everything wet. In this embodiment, the nozzles 20 can even be omitted and small drain holes 62 can be provided directly in floor 17 of reservoir 4, as shown in FIG. 13. As noted, the dissolving cup 8 is provided in association with the reservoir 4 so that water can flow from the reservoir 4 to the dissolving cup 8 to dissolve a shower tablet or fragrance carrier in the cup 8.

Figure 14:
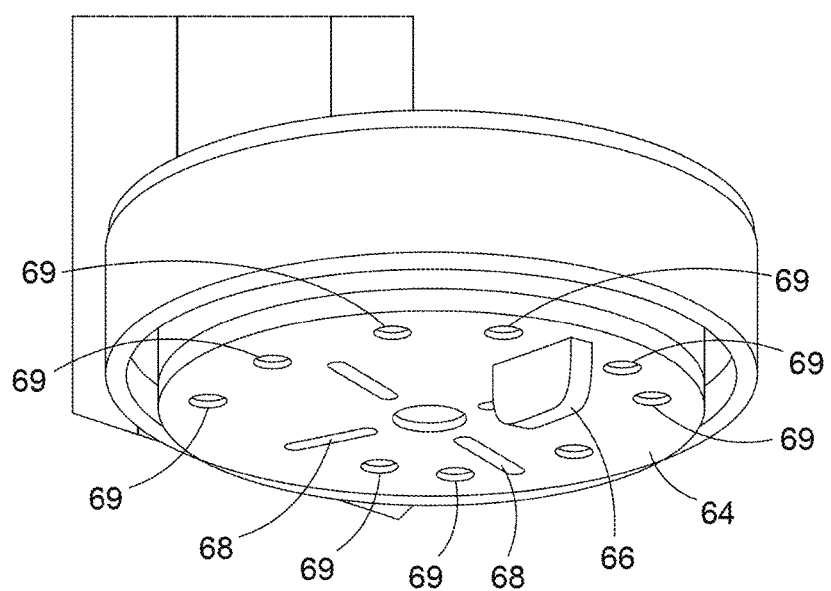
FIG. 14 is an alternative embodiment of a valve of the reservoir.

Alternatively, in place of valve 22, a rotatable flow regulator valve 64 (see FIG. 14) can be attached immediately beneath floor 17 (whether floor 17 has holes 62 or nozzles 20). Valve 64 is provided with drainage slots or openings 68 and/or drainage holes or openings 69 (located at predetermined positions) and a finger tab 66. In a first position or orientation, valve 64 blocks all holes 62, so no water flows. Then valve 64 is rotated via finger tab 66 to a second position, where the openings 68, 69 line up with some of the holes 62, so some water flows. Then valve 64 is rotated to a third position, where the openings 68, 69 line up with all the holes 62, so maximum flow is permitted. In this way, the volume of flow can be controlled or regulated. Less preferably, valve 64 can be fixed in position and non-rotatable, but reservoir 4 can be rotated by the user so that none or some or all of the holes 62 line up with the openings 68, 69. Other rotatable flow regulator valves known in the art can be used.

Figure 15:
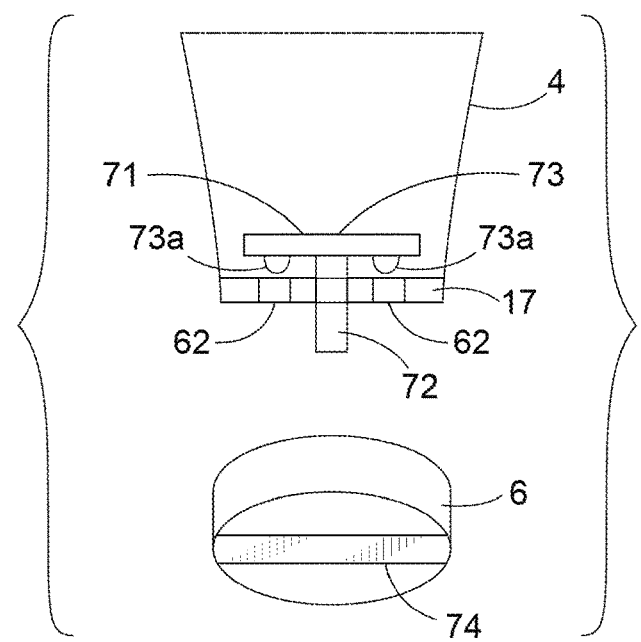
FIG. 15 is a schematic exploded view illustration of an alternative embodiment of a valve for the reservoir.

Alternatively, a poppet valve can be used. With reference to FIG. 15, the bottom or floor 17 of the reservoir 4 has a plurality of holes 62 (compare with FIG. 13). A spring-loaded poppet valve 71, having a post 72, is provided. A spring attached to the post 72 biases the cap 73 of the poppet valve 71 in the closed position, so that the knobs or bumps 73a plug or seal the holes 62. When the reservoir 4 is seated in the support bracket 6, the bottom of the post 72 contacts the center of a crosspiece 74 fixed at the bottom of the support bracket 6 and forces the cap 73 upwards, so that the spring is compressed and the valve 71 is opened and the holes 62 are unsealed and water can flow through. Perforations can also be provided at selected locations through the cap 73 and through the crosspiece 74. Other poppet valves known in the art can be used.

Figure 16:
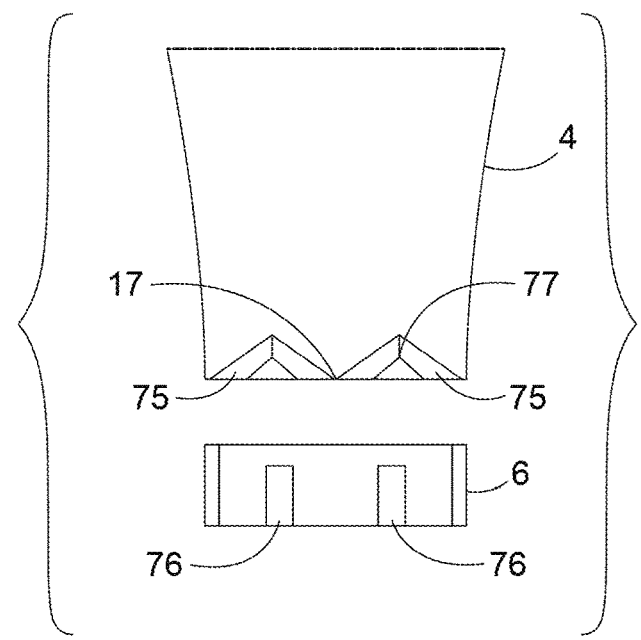
FIG. 16 is a schematic exploded view illustration of an alternative embodiment of a valve for the reservoir.

Alternatively, one or more duckbill valves can be used. With reference to FIG. 16, the bottom or floor 17 of the reservoir 4 is provided with one or more duckbill valves 75. A duckbill valve is known in the art and is designed to normally allow flow in one direction. At the top or tip of each duckbill valve 75 is an opening or slit 77, which is normally resiliently closed. When the reservoir 4 is seated in the support bracket 6 (see exploded view in FIG. 16), there is a hollow tube 76 fixed to the bottom of bracket 6 directly beneath each valve 75, which punches or stabs or forces its way through the resilient opening or slit 77 of the valve 75 when the reservoir 4 is pushed down and seated in bracket 6. The water in the reservoir 4 then flows into and through the tube 76 and out the bottom, onto the fragrance carrier or tablet 48. Alternatively, a vertical spike or prong with a plurality of outwardly extending vertical longitudinal ribs or fins (creating vertical and longitudinal drainage or flow channels) can be substituted for each tube 76. Other duckbill valves known in the art can be used.

Other valves can be used. For example, the rotatable flow regulator valve 64 of FIG. 14 can be mounted to the bottom of floor 17 of FIG. 15 so that the flow of the water released by the poppet valve 71 can be regulated. Also, with reference to FIG. 15, duckbill valves 75 can be provided on/through floor 17 and corresponding hollow tubes 76 can be mounted on crosspiece 74 (which can be larger and perforated). Also, with reference to FIG. 16, a plurality of duckbill valves 75 can be provided, with some being taller, some being shorter and others of in-between heights; and/or a plurality of hollow tubes (such as tubes 76) can be provided, of same or different heights. When the reservoir 4 is in a first orientation (i.e., facing "noon"), all or most of the tubes open all or most of the valves; in a second orientation (i.e., facing "3 PM"), only some of the tubes open some of the valves; in a third orientation (i.e., facing "6 PM"), none of the valves are opened. In this manner, volume of flow can be controlled. Other valves known in the art can be used to control or at least partially control flow from reservoir 4. The valves described above control or at least partially control the flow of water from the reservoir 4.

Figure 17:
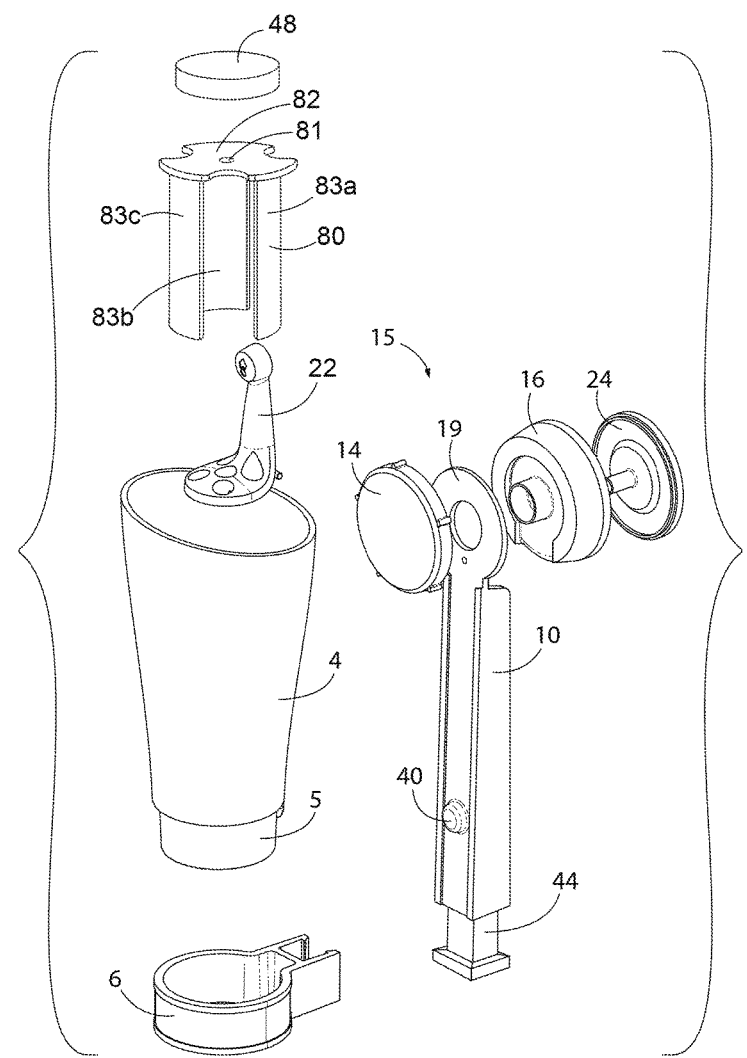
FIG. 17 is an exploded view illustrating an alternative embodiment of a fragrance carrier holder.
Figure 18:
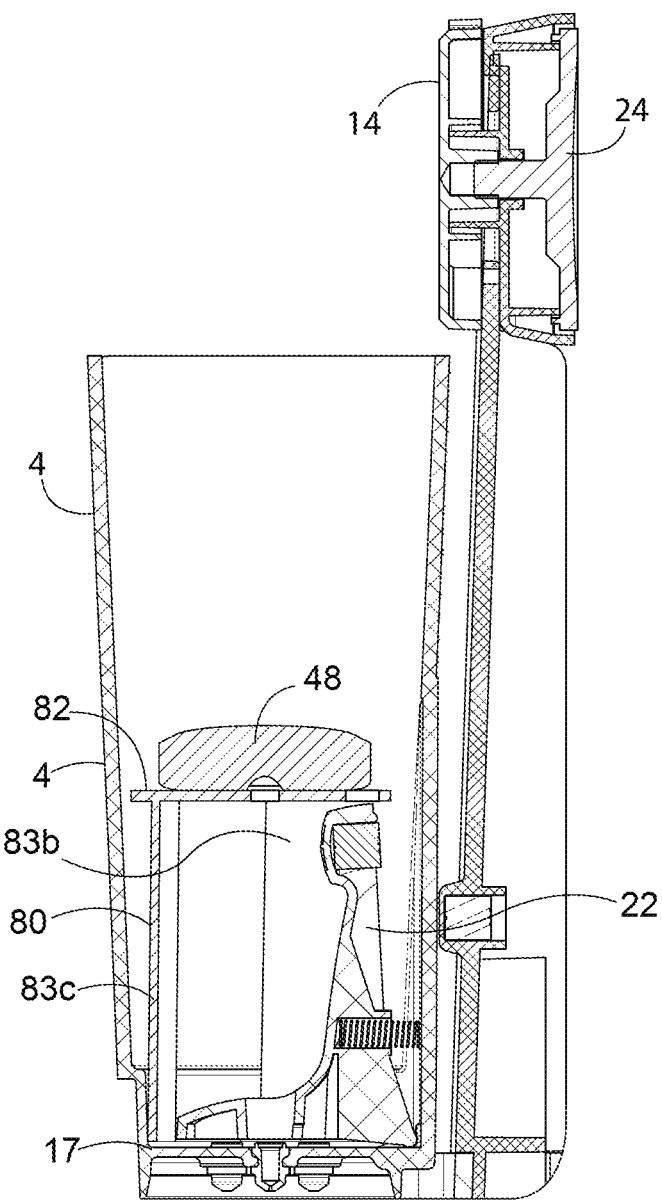
FIG. 18 is a cross-sectional view similar to FIG. 7 showing the fragrance carrier holder and shower tablet of FIG. 17 inside the reservoir.

With reference to FIGS. 17 and 18, there is shown a fragrance carrier holder 80 (which supports the fragrance carrier or tablet 48 off or above the floor 17) having a top shelf or shelf 82 (the top of which is optionally or preferably less than 1, 2, 3, 4, 5 or 6 cm above floor 17), three legs 83a, 83b and 83c and a drain hole 81. Optionally, a protrusion 50 can be provided in place of drain hole 81; optionally perforations like drain holes 62 can be provided in shelf 82. In use, fragrance carrier holder 80 is seated on floor 17 (FIG. 18) straddling around valve 22; fragrance carrier or tablet 48 is placed or dropped onto shelf 82 before or after reservoir 4 is filled with water; tablet 48 is immersed in the water; the reservoir 4 is seated in bracket 10 so that the valve (such as valve 22) is opened; the fragrance carrier or tablet 48 dissolves in the water and the water flows out the bottom of the reservoir 4. Alternatively, there can be no valve and bottom or floor 17 can just have nozzles 20 or drain openings or drain holes like drain holes 62, or floor 17 can have no nozzles or drain holes or openings, in which case the water does not flow out—in this case, after the fragrance carrier or tablet 48 has dissolved on the shelf 82 the user grabs reservoir 4 and empties or pours its water onto the shower floor or into the bathtub, etc.

Alternatively, the apparatus 2 can have no fragrance carrier holder, inside or outside. In this embodiment, the fragrance carrier or tablet 48 is dropped into reservoir 4 and the valve opens as usual. Alternatively, there can be no valve but there can be openings such as nozzles or holes 62; alternatively, there can be no valve or openings; in this case, after the fragrance carrier or tablet 48 is put in and dissolves, the user empties the water out of the reservoir 4.

With reference to FIGS. 29-40, there is shown an apparatus 102A accordingly to a further embodiment of the invention. Apparatus 102A is preferably the same as apparatus 2 except for the differences of apparatus 102A illustrated and explained herein. Less preferably, apparatus 102A can have different modifications according to features and materials known in the art. The apparatus 102A comprises a water-holding reservoir 104A, a mount bracket 110, a wall mount 115, a reservoir support bracket 106A, a fragrance carrier holder or dissolving cup 108A and a fragrance carrier holder support bracket or dissolving cup support bracket 112. The mount bracket 110 comprises the reservoir support bracket 106A and the fragrance carrier holder support bracket or dissolving cup support bracket 112. The wall mount 115 can be integral with or part of the mount bracket 110, or separate from mount bracket 110. The mount bracket 110 can be provided with a wall mount 115. The reservoir 104A is supported by the mount bracket 110 and has an opening 103A at the top and a narrowed portion 105A at the bottom to engage and seat in the reservoir support bracket 106A. Alternatively, support bracket 106A can engage reservoir 104A higher up, such as half-way up reservoir 104A, for example, via a narrowed portion or via another attachment mechanism.

The bottom of reservoir 104A can be provided with a valve, such as valve 122, as described later. Support bracket 106A has an engagement portion 107a which is inserted into cavity 107b and secured to mount bracket 110 via screw 107c. Fragrance carrier holder support bracket 112 has an engagement portion 112a which is inserted into cavity 112b and secured to mount bracket 110 via screw 112c. Alternatively, brackets 106A and 112 can be integrally molded with bracket 110 or attached via other means as known in the art.

Scraper 139 is removably clipped into the back side of mount bracket 110 (see FIGS. 29, 31, 32) via plastic clips at locations or openings 140, 141, 141. At location 140c on mount bracket 110 a flexible finger 140a extends horizontally having at its tip a downwardly extending tongue or ledge; the finger 140a extends through scraper opening 140 and the ledge clips or extends over the bottom edge 140b of opening 140. At each of locations or openings 141, 141 there is a similar or corresponding mount bracket 110 flexible finger having at its tip an upwardly extending tongue or ledge; each such finger extends through the respective opening 141, 141 and the ledge clips or extends over the top edge of the opening 141. To disengage the scraper 139, push up on the scraper to disengage the clipping ledges at 141, 141; then push the scraper 139 down to disengage the ledge of finger 140a. Other plastic clip engagements known in the art can be used. Plastic scraper 139 can be used to scrape off adhesive element 152 from the wall when needed.

Figure 31:
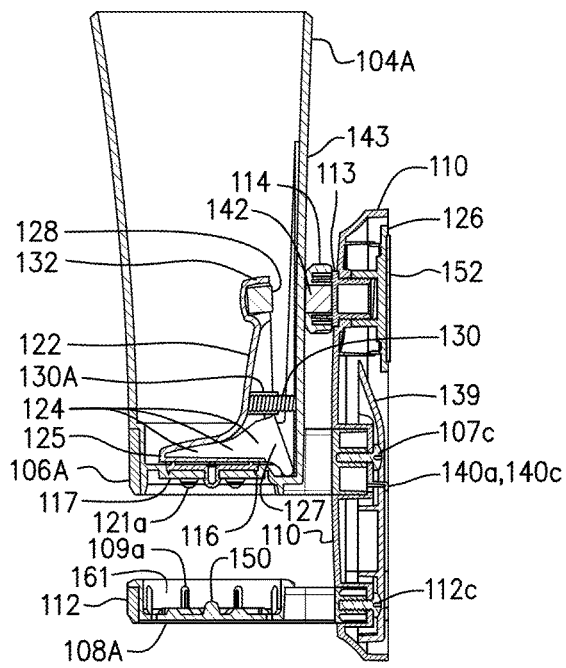
FIG. 31 is a cross-sectional view taken along line 31-31 of FIG. 30.
Figure 32:
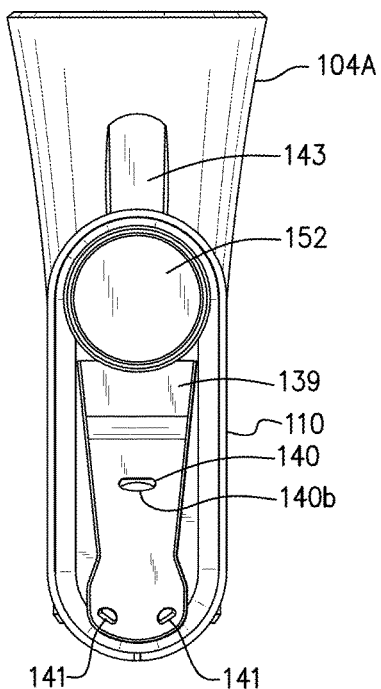
FIG. 32 is a back view of the apparatus of FIG. 30.

Wall mount 115 includes knob 114, threaded link 113, mount anchor 126 and adhesive element or strip or disc 152. Mount bracket magnet or second magnet 142 is located in knob 114 as shown in FIG. 31; knob 114 can be removably fixed to threaded link 113 via friction and/or interference engagement, preferably with interlocking longitudinal ribs so that link 113 rotates when knob 114 is rotated; alternatively, knob 114 can be non-removably fixed to link 113 via adhesive, melting of plastic or other means known in the art, with magnet 142 sealed inside. Adhesive element or disc 152 is preferably a double-sided adhesive strip as known in the art or other thin plastic strip or disc, preferably foam. Disc 152 is preferably adhesively attached to the flat back surface of mount anchor 126. Both surfaces of disc 152 are preferably coated with very high bond adhesive as known in the art. Disc 152 is preferably made of VHB (Very High Bond) double-sided acrylic or modified acrylic adhesive foam tape available from 3M Company. Other very high bond tapes can be used. Disc 152 can be attached via other adhesives. For example, a combination of double-sided adhesive foam and silicone sealant or adhesive or glue, such as Loctite Clear Silicone Waterproof Sealant, can be used. For example, the silicone sealant or adhesive or glue can be placed between the double-sided adhesive foam and the shower wall for extra bonding power. The apparatus 102A preferably when sold to the consumer has a release liner covering the exposed adhesive surface of disc 152; the release liner is removed by the consumer and mount anchor 126 is pressed against the vertical surface of the shower stall or wall above the bathtub where intended by the consumer.

To mount the mount bracket 110, after mount anchor 126 is attached to the wall, the externally threaded portion 113b of link 113 is inserted through hole or opening 118 and rotated via knob 114 so that externally threaded portion 113b is screwed into internally threaded post 126a to securely fasten bracket 110 to mount anchor 126.

Nozzle-holding seal 120 comprises five nozzles 121, four standoffs 136 and a perimeter rim 119 in the shape of an upside down V which extends upwardly at an about 45° angle as shown. Preferably the entirety of seal 120 including the nozzles 121, standoffs 136 and rim 119 is monolithic and unitary and is made of silicone rubber, less preferably other elastomeric material. Each nozzle has a bottom 121a and has a central bore with a diameter as described above for nozzles 20.

Reservoir 104A has a bottom or floor 117 which preferably is solid and which seals the bottom of reservoir 104A except that it is provided with five holes through which extend the five nozzles 121. When seal 120 is installed in floor 117, the nozzles 121 are forced through the holes in floor 117 and an extending annular shoulder rib 129 near the bottom 121a of each nozzle 121 helps to seal the nozzle 121 in the hole and tends to resist or restrain nozzle 121 going back out through the hole; also, a circumferential V-shaped rib 116 extending downwardly beneath rim 119 is inserted or forced into a corresponding V-shaped gland 116a in the top of floor 117.

When the flat bottom 146 of valve 122 pushes against seal 120, the rim 119 is deflected or forced downwardly and radially outwardly until the bottom 146 engages the four upwardly extending standoffs 136 which extend upwardly an effective distance for bottom 146 to compress rim 119 enough to seal the entire rim 119 against bottom 146 but not too much to over-flatten rim 119. This seals the bottom of reservoir 104A and prevents water from getting to the nozzles 121.

Figure 29:
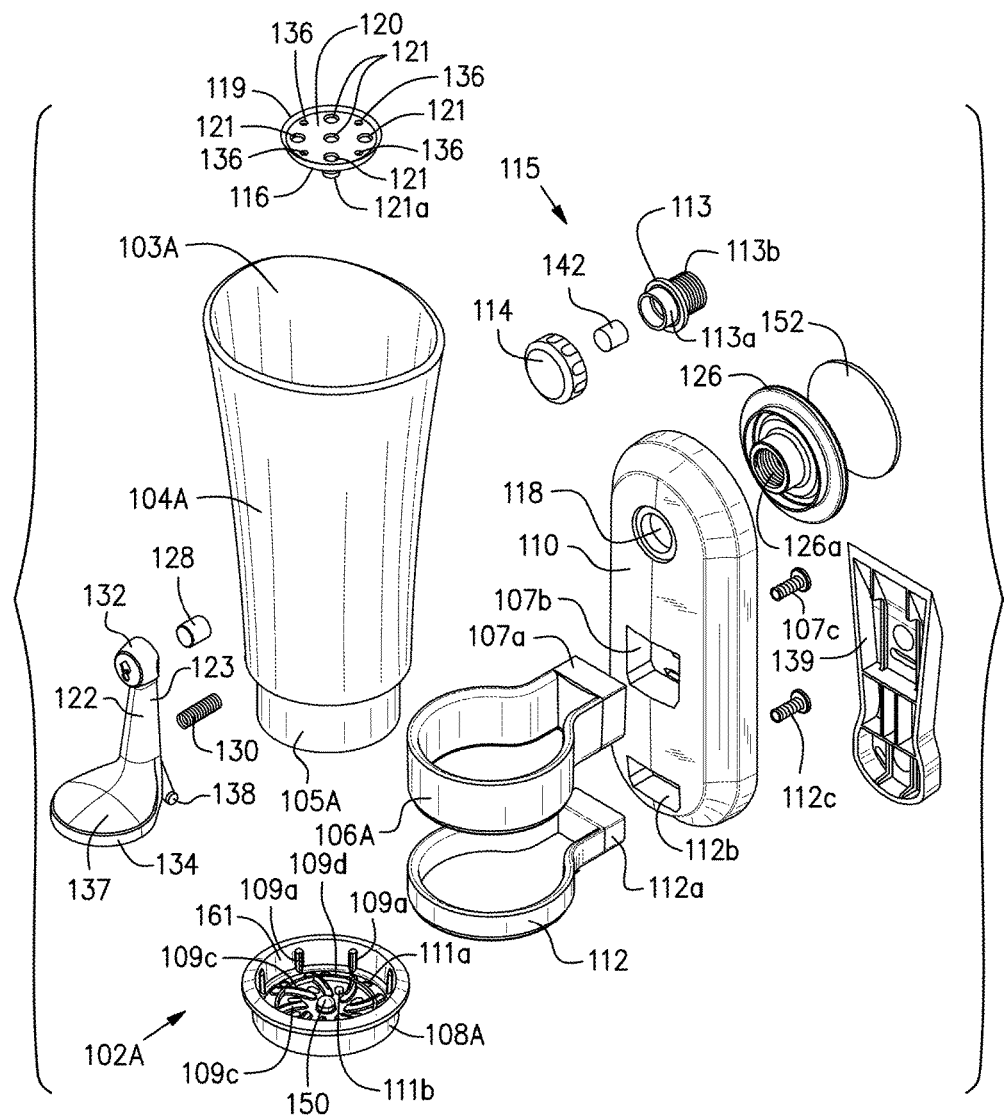
FIG. 29 is an exploded view of an apparatus according to a further embodiment of the invention.
Figure 30:
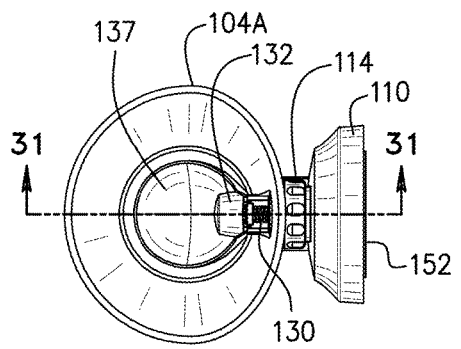
FIG. 30 is a top plan view of the apparatus of FIG. 29 in an assembled condition.
Figure 33:
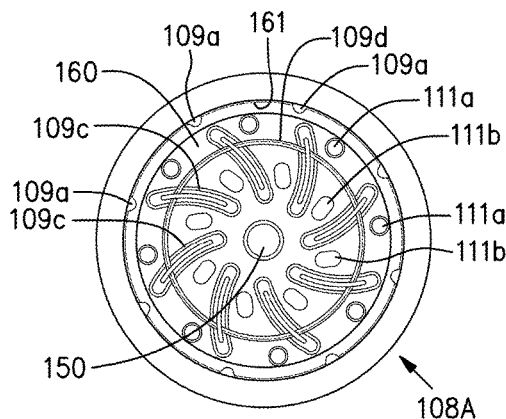
FIG. 33 is a top plan view of the dissolving cup of FIG. 29.

With reference to FIGS. 29, 31 and 33, dissolving cup 108A has a floor 160 and an inner perimeter wall 161. Along wall 161 are provided a plurality of ribs or standoffs 109a; on the floor 160 are provided a plurality of ribs or standoffs 109c and a circular rib or standoff 109d. Drain holes or openings 111a and 111b are provided through floor 160. A central protrusion or dome or bump or post or knob 150 extends upwardly from floor 160. The features of cup 108A are sized the same as and/or correspond to the features of dissolving cup 8 described above.

With respect to FIGS. 29-31 and 38-40, there is shown a valve or flapper valve 122 which comprises a central portion 123, a foot or flapper foot or valve foot 134 and a pair of pivots 138. A valve magnet housing 132 is provided at the top of the central portion 123; a valve magnet or first magnet 128 is constrained or fixed in the housing 132. (Alternatively, instead of two magnets 128 and 142, one or the other can be a non-magnetized piece of iron-containing material, such as a piece of iron or steel, which will simply act as an attraction element to attract the other magnet.) The foot 134 has a tip or toe 125 and has a top 137 which preferably seals the front portion of the foot 134 so that water can only enter through the back 127 to fill the cavity 124 with water. Each pivot 138 snaps into or otherwise engages a corresponding pivot seating 138*a* so that flapper valve 122 is fixed inside and near the bottom of reservoir 104A and can rotate clockwise/counterclockwise with reference to FIG. 31. Valve 122 comprises a spring housing 130A within which is housed or fixed a portion of a spring 130 so that valve 122 is spring-biased or spring-loaded such that, when the reservoir 104A is removed from the reservoir support bracket 106A (such as for refilling with water), the spring 130 pushes against the wall of reservoir 104A and urges the valve 122 to rotate until it closes and clampingly seals the bottom 146 against the seal 120. The bottom 146 of valve 122 is preferably about 1-2 or 1-3 mm thick and is preferably hard or rigid plastic; less preferably a resilient and/or elastomeric material.

As shown most clearly in FIG. 37 and also with reference to FIGS. 31, 32 and 34-36, the back of the reservoir 104A is provided with a slot 145 defined by a longitudinal bulge 143 extending outwardly from the back of the reservoir 104A to help provide room for and define the slot 145 on the inside. The slot 145 has a back 144. The presence of the slot 145 provides a little additional room for the valve 122 to rotate clockwise and counterclockwise (see FIG. 31) and for the first magnet 128 to approach more closely to the second magnet 142. (The two magnets 128, 142 are arranged so they attract each other). The flapper valve 122 operates basically in the same manner as flapper valve 22 described above, except that when the reservoir 104A is filled with water, the water will immediately enter and fill cavity 124 through the open back 127. When the user then seats or mounts the reservoir 104A in or on the support bracket 106A, the first magnet 128 will move towards the second magnet 142, overcoming the resistance of spring 130 and tilting and opening the valve 122 so that water can then flow out through the nozzles 121. Simultaneously, since the foot 134 will now be tilted backwards a little bit, the water in cavity 124 can drain out through back 127.

In preferred embodiments, all of the alternative and optional features of apparatus 2 described above can also be alternative and optional features for the apparatus 102A, such as optional or alternative valves, nozzles, magnets, materials, dimensions, mount brackets, wall mounts, support brackets, fragrance carrier holders, dissolving cups, etc. Alternatively, either apparatus 2 or apparatus 102A can be fitted with a base or stand so that it can stand upright and be free-standing on the floor of the shower or bathtub. Less preferably, either apparatus 2 or apparatus 102A can be hung from a hook on the wall or ceiling, or be hung by a hook or string or wire, etc. from something in the shower stall or bathtub area.

Although the hereinabove described embodiments of the invention constitute the preferred embodiments, it should be understood that modifications can be made thereto without departing from the scope of the invention as set forth in the appended claims.

What is claimed is:

1. An apparatus for dissolving a fragrance carrier, the apparatus comprising a mount bracket, a water-holding reservoir and a fragrance carrier holder, the water-holding reservoir being supported by the mount bracket, the fragrance carrier holder being provided in association with the water-holding reservoir such that (a) water in the water-holding reservoir can contact and dissolve a fragrance carrier located on the fragrance carrier holder, the fragrance carrier holder being located inside the water-holding reservoir, or (b) water can flow from the water-holding reservoir to contact and dissolve a fragrance carrier located on the fragrance carrier holder, the apparatus being configured and adapted so that it is attachable to a vertical wall of a shower stall by adhesive.

2. The apparatus of claim 1, wherein the fragrance carrier holder is provided outside the water-holding reservoir such that water can flow from the water-holding reservoir to contact and dissolve a fragrance carrier located on the fragrance carrier holder.

3. The apparatus of claim 2, wherein the fragrance carrier holder is supported by the mount bracket and wherein the fragrance carrier holder is located such that a fragrance carrier located on the fragrance carrier holder will be located beneath the water-holding reservoir.

4. The apparatus of claim 3, wherein a nozzle-holding seal comprising a plurality of nozzles is installed in a floor of the water-holding reservoir.

5. The apparatus of claim 1, wherein a plurality of nozzles are provided at a floor of the water-holding reservoir.

6. The apparatus of claim 1, wherein the mount bracket is provided with a wall mount, wherein the wall mount comprises an adhesive-coated surface effective to adhesively attach the wall mount to a vertical wall of a shower stall.

7. The apparatus of claim 6, wherein the wall mount includes a knob, a magnet or attraction element being provided in the knob.

8. The apparatus of claim 6, wherein the adhesive-coated surface is coated with very high bond adhesive.

9. The apparatus of claim 6, wherein the adhesive-coated surface is on a double-sided adhesive strip or disc.

10. The apparatus of claim 1, wherein the mount bracket comprises (a) a reservoir support bracket which supports the water-holding reservoir and (b) a fragrance carrier holder support bracket which supports the fragrance carrier holder.

11. The apparatus of claim 1, wherein a floor or shelf of the fragrance carrier holder is provided with a central protrusion.

12. The apparatus of claim 1, wherein the water-holding reservoir is provided with a valve which is effective to at least partially control flow of water from the water-holding reservoir.

13. The apparatus of claim 12, wherein the valve is a flapper valve.

14. The apparatus of claim 12, wherein the valve has a first magnet or first attraction element and wherein a second magnet or second attraction element is provided with the mount bracket or with a wall mount connected to the mount bracket such that (1) when the water-holding reservoir is removed from the mount bracket, the valve is biased in a closed position to prevent water from flowing out of the water-holding reservoir, and (2) when the water-holding reservoir is mounted in or on or with the mount bracket, magnetic attraction between (a) one of the magnets and (b) the other magnet or one of the attraction elements causes the valve to go to an open position to permit water to flow out of the water-holding reservoir.

15. The apparatus of claim 12, wherein (a) the valve has a first magnet and an attraction element is provided with the mount bracket or with a wall mount connected to the mount bracket, or (b) the valve has an attraction element and a magnet is provided with the mount bracket or with a wall mount connected to the mount bracket, or (c) the valve has a first magnet and a second magnet is provided with the mount bracket or with a wall mount connected to the mount bracket.

16. The apparatus of claim 1, wherein a shower tablet is located on the fragrance carrier holder.

17. The apparatus of claim 1, further comprising a scraper removably attached to the mount bracket.

18. A method for dissolving a fragrance carrier in a shower or bathtub, comprising the following steps:
   a) providing a mount bracket mounted via adhesive in a shower stall or in or above a bathtub;
   b) at least partially filling a water-holding reservoir with water;
   c) before or after said filling step, mounting the water-holding reservoir in or on or with said mount bracket;
   d) contacting a fragrance carrier with water in or from the water-holding reservoir until the fragrance carrier is at least substantially dissolved.

19. The method of claim 18, wherein the fragrance carrier is a shower tablet and is located on a fragrance carrier holder, wherein the fragrance carrier holder is provided outside the water-holding reservoir such that water can flow from the water-holding reservoir to contact and dissolve the fragrance carrier.

20. The method of claim 19, wherein a floor of the fragrance carrier holder is provided with a central protrusion.

21. The method of claim 18, wherein the water-holding reservoir is provided with a valve which is effective to at least partially control flow of water from the water-holding reservoir.

22. The method of claim 21, wherein the valve has a first magnet or first attraction element and wherein a second magnet or second attraction element is provided with the mount bracket or with a wall mount connected to the mount bracket such that (1) when the water-holding reservoir is removed from the mount bracket, the valve is biased in a closed position to prevent water from flowing out of the water-holding reservoir, and (2) when the water-holding reservoir is mounted in or on or with the mount bracket, magnetic attraction between (a) one of the magnets and (b) the other magnet or one of the attraction elements causes the valve to go to an open position to permit water to flow out of the water-holding reservoir.

23. The method of claim 21, wherein (a) the valve has a first magnet and an attraction element is provided with the mount bracket or with a wall mount connected to the mount bracket, or (b) the valve has an attraction element and a magnet is provided with the mount bracket or with a wall mount connected to the mount bracket, or (c) the valve has a first magnet and a second magnet is provided with the mount bracket or with a wall mount connected to the mount bracket.

24. The method of claim 18, wherein the fragrance carrier is a shower tablet.

* * * * *